United States Patent [19]

Tobe et al.

[11] Patent Number: 5,679,716
[45] Date of Patent: Oct. 21, 1997

[54] PHARMACEUTICAL COMPOSITION FOR TREATING OSTEOPOROSIS

[75] Inventors: Hiroyasu Tobe, Fujisawa; Kazuyuki Kitamura, Sakado; Osamu Komiyama, Higashimurayama, all of Japan

[73] Assignee: Hoechst Japan Limited, Tokyo, Japan

[21] Appl. No.: 720,004

[22] Filed: Sep. 27, 1996

Related U.S. Application Data

[62] Division of Ser. No. 424,644, Apr. 19, 1995, abandoned.

[30] Foreign Application Priority Data

Apr. 21, 1994 [JP] Japan ..................... 6-82852

[51] Int. Cl.$^6$ ..................... A01N 35/00; A61K 31/11
[52] U.S. Cl. ..................... 514/685; 514/687
[58] Field of Search ..................... 514/687, 685

[56] References Cited

U.S. PATENT DOCUMENTS 3,794,744 2/1974 Gardner ..................... 426/424
4,065,574 12/1977 Moon et al. ..................... 424/283

OTHER PUBLICATIONS

Chemical Abstracts 106:135069, "A New Flavanone w Antifungal Activity Isolated From Hops", Mizobuchi et al. 1985.
Mizobuchi et al., "A New Flavanone with Antifungal Activity Isolated From Hops," Rep. Res. Lab. Kirin Brew. Co., 28:33–38 (1985).
Chury, J., "Über Den Phytoöstrogengehalt Einiger Pflanzen," Experientia 16:194–95 (1960) (with English Translation).
Koch et al., "Östrogene Hormone in Hopfen Und Bier," Münch. Med. Wschr. 95:845 (1953) (with English Translation).
Iwasa et al., "The Role of Female Sex Hormone in Osteoporosis—Effect of Whole Bone Metabolism," Journal of Clinical and Experimental Medicine 165(9):533–37 (1993) (with English Translation).
Fenselau et al., "Is Oestrogenic Activity Present in Hops?", Food Cosmet. Toxicol. 11:597–603 (1973).
Hoffman, B., "A Modified Detection Reaction for Oestrogens on Paper Chromatograms and Thin Layer Chromatograms," J. Chromatog. 34:269 (1968) (with English Translation).
Mizobuchi et al., "Antifungal Activities of Hop Bitter Resins and Related Compounds," Agric. Biol. Chem. 49(2):399–403 (1985).
Verzele et al., "Xanthohumol, A New Natural Chalkone," Bull. Soc. Chim. Belg. 66:452–75 (1957).
Hänsel et al., "Demethylxanthohumol: Isolation from Hops and Cyclization to Flavanones," Arch. Pharm. (Weinheim) 321:37–40 (1988) (with English Translation).
Chemical Abstracts, 102:75700, "A New Flavanone with Antifungal Activity Isolated From Hops" Agric. Biol. Chem. (1984), 48(11), 2771–5.
Hölzl et al., "Inhaltsstoffe Des Hopfens," Zeitschrift für Phytotherapie 13(5):155–61 (1992) (with English Translation).

Primary Examiner—Frederick Krass
Attorney, Agent, or Firm—Finnegan, Henderson, Farabow, Garrett & Dunner, L.L.P.

[57] ABSTRACT

A therapeutic agent for osteoporosis comprising as an active ingredient xanthohumol. Xanthohumol obtained from hop extracts has a bone resorption inhibiting activity and is useful as a therapeutic agent for osteoporosis.

1 Claim, No Drawings

PHARMACEUTICAL COMPOSITION FOR TREATING OSTEOPOROSIS

This application is a division of application Ser. No. 08/424,644, filed Apr. 19, 1995, now abandoned.

This invention relates to a pharmaceutical composition for treating osteoporosis.

Japan is now rushing into an advanced age society which has never been experienced in the past, and simultaneously the increase in the number of osteoporotic patients now becomes a serious problem. The increased number of the aged who are bedridden due to bone fracture compels an enormous increase in medical expenditures.

As a therapeutic agent for osteoporosis, vitamin D preparations, calcitonin preparations, ipriflavone preparations and the like have been used in Japan. However, there has not been established a method for radically treating osteoporosis, but simply a symptomatic treatment is applied at this stage. Osteoporosis develops when a balance between bone formation and bone resorption is lost, and consequently it is considered feasible to prevent osteoporosis by promoting bone formation or by inhibiting bone resorption.

An object of the present invention is to provide a novel pharmaceutical composition for treating osteoporosis. The present inventors have found, as a result of various studies, the fact that xanthohumol contained in hop extracts has a strong inhibiting activity against bone resorption, and this invention has been now completed.

Hops (*Humulus lupulus* L.) have been originally known as a medical herb and have long been used for brewing of beer. Thus, xanthohumol can be said to be of sufficiently low toxicity.

This invention comprises a pharmaceutical composition for treating osteoporosis containing as an active ingredient xanthohumol having the formula (1).

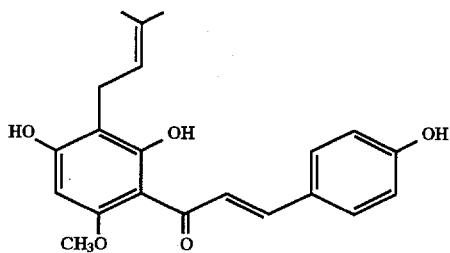

(1)

The present inventors have attempted to develop a therapeutic agent for osteoporosis and carried out the screening tests for substances to inhibit bone resorption.

On the other hand, as one of the bone resorption inhibiting factors, a female sex hormone, estrogen, has been hitherto reported [IGAKU NO AYUMI (Journal of Clinical and Experimental Medicine), (1993), Vol. 165, p. 533] and it has been actually used as a therapeutic agent for osteoporosis in Europe and the North America. However, the estrogen therapy may cause side effects including hyperplasia of endometrium, genital hemorrhage, mastodynia, obesity, onset of cancer of endometrium and the like and it has been desired to discover a compound having an estrogenic activity without side effects. Therefore, the present inventors have paid their attention to the report that the hop extracts contain an estrogenic substance and that the active part of the substance has not yet been elucidated [Food Cosmet. Toxicol., (1973), Vol. 11, p. 597–603], and they have performed purification of such an estrogenic substance and assay of its bone resorption inhibiting activity by means of pit formation assay. As a result, it was found that xanthohumol inhibits bone resorption at a concentration of as low as up to $10^{-6}$M. The fact that xanthohumol possesses the pit formation inhibiting activity had not been reported so far it was firstly elucidated by the present invention.

For identifying an estrogenic substance from the hop extracts, phosphomolybdic acid, a color reagent which reacts specifically with estrogen, [J. Chromatog., (1968), Vol. 34, p. 269] was found effective and therefore said color reagent was used as an identification reagent for the estrogenic substance which was colored green.

Xanthohumol can be prepared by purification from natural hops and also by chemical synthesis according to a traditional method.

The dosage in clinical use is, though it varies depending on an administration method, normally within a range of 0.1 g–2 g per adult per day as xanthohumol (about 1.5 mg –30 mg/kg/day). It can be administered intravenously, intramuscularly, orally and intrarectally. In case of an intravenous administration, an intravenous drip can be applied in addition to a normal intravenous injections.

The preparations containing xanthohumol are manufactured by an ordinary method using ordinary excipients and additives.

Injectable preparations can be formulated, for example, in the form of injectable powders. In that case, the powders can be prepared by adding one or more of suitable water soluble excipients such as mannitol, sucrose, lactose, maltose, glucose, fructose and the like, to an active ingredient, dissolving the mixture in water, dividing it into vials or ampoules followed by lyophilizing and sealing.

As an oral preparation, it can be formulated in the form of ordinary tablets, capsules, granules, fine granules or powders as well as enteric preparations.

Enteric preparations can be prepared by adding to an active ingredient excipients such as mannitol, sucrose, lactose, maltose, starch, silicic anhydride, calcium phosphate and the like, lubricants such as talc, magnesium stearate and the like, binders such as carboxymethyl cellulose, methyl cellulose, gelatin, gum arabic and the like and disintegrators such as calcium carboxymethyl cellulose and the like, if necessary, to prepare tablets, granules, fine granules and the like, to which are further added one or more of enteric bases such as cellulose acetate phthalate, hydroxypropylmethyl cellulose phthalate, hydroxypropylmethyl cellulose acetyl succinate, polyvinyl alcohol phthalate, styrene-maleic anhydride copolymer, styrene-maleic acid copolymer, methyl methacrylate-methacrylic acid copolymer, methyl acrylate-methacrylic acid copolymer and if necessary, a coloring agent such as titanium oxide to prepare coated preparations. The enteric granules or fine granules prepared above can be encapsulated to prepare capsules.

Moreover, capsules prepared according to an ordinary method can be coated with the afore-mentioned enteric bases to prepare enteric capsules. Alternatively, enteric capsules can be prepared by using a capsule made from the afore-mentioned enteric bases alone or in admixture with gelatin.

Depositories can be prepared by adding to an active ingredient a lipophilic base such as a semi-synthesized base wherein cacao butter or fatty acid triglyceride are blended with fatty acid monoglyceride or fatty acid diglyceride in various ratios, or hydrophilic base such as polyethylene glycol and glycerogelatin and the like, dissolved by heating, to give a homogeneous blend and then pouring the blend into a mold to prepare a suppository.

This invention shall be more illustratively explained by way of the following examples.

EXAMPLE

Example 1

(1) Purification of Xanthohumol from Hops

To 250 g of commercially available hops (purchased from Rupofresh Co., Inc.) was added 500 ml of acetone and the percolation and extraction procedures over one hour were repeated three times in total. The resulting acetone extract was concentrated under reduced pressure to give 50 g of black syrup. A portion of the resulting syrup (17.5 g) was dissolved in 500 ml of 0.5% acetic acid/80% methanol and developed on an anion exchange resin Dowex-I (cross linking degree×4, particle size 200–400 mesh, acetic acid type, The Dow Chemical Co.) using a column (5 cm diameter×27.5 cm length) at a flow rate of 3 ml/minute.

The adsorbed hop extract was gradiently eluted with a mixture of acetic acid and methanol according to the literature (Agric. Biol. Chem., (1985), Vol. 49, p. 399–403) and the eluate was fractionated to 10 g portions on the liquid weight by means of a fraction collector. First, 1 lit. of 0.5% acetic acid/80% methanol and then 2 lit. of 5% acetic acid/80% methanol were added from the top of the column to elute insoluble materials and then xanthohumol was extracted with 1 lit. of 20% acetic acid/80% methanol.

Sampling of each 10 µl was performed from the fraction Nos. 1-420 of those fractions fractionated in each 10 g and the samples were spotted over a silica gel thin layer (Silica gel plate No. 5715 available from Merck AG), which was then developed with a mixed organic solvent (ethyl acetate:methanol=30:1). A 4% methanolic solution of phosphomolybdic acid (purchased from Merck AG) as a color reaction liquid for the phenolic hydroxy group was sprayed over the silica gel plate, which was then brought into contact with gaseous ammonia to perform coloration. Xanthohumol was colored green and this coloring reaction was applied to identification of xanthohumol over the silica gel plate.

As a result, xanthohumol was eluted in the fractions having the fraction Nos. 320–400 eluted from the Dowex-1 column chromatography. The fractions were concentrated under reduced pressure to give 80 mg of a powdery substance. Accordingly, 90.7 mg of xanthohumol was calculated to yield per 100 g of hops.

(2) Structural Determination of Xanthohumol

The structure of the xanthohumol thus fractionated and purified was investigated by means of color reaction, proton and $^{13}C$ nuclear magnetic resonance spectra, mass spectrum and infrared absorption spectrum.

(3) Color Reaction of Xanthohumol using Ferric Chloride ($FeCl_3$)

A 2% $FeCl_3$ (purchased from Wako Pure Chemicals Ltd.) in ethanol was sprayed onto xanthohumol on a silica gel plate to develop a similar yellow tone to that disclosed in the literature (Bull. Soc. Chim. Belg., (1957), Vol. 66, p. 452–457). Accordingly, coloration of the present xanthohumol was in agreement with that disclosed in the literature.

(4) $^1H$-NMR Spectrum (internal standard: TMS)

$^1H$-NMR δ ($CD_3OD$): 1.648 (3H, s), 1.755 (3H, s), 3.223 (2H, d), 3.896 (3H, s), 5.196 (1H, t), 6.004 (1H, s), 6.819 (2H, d), 7.493 (2H, d), 7.646 (1H, d), 7.799 (1H, d)

These values are in agreement with those disclosed in the literature (Arch. Pharm., Weinheim, 1988, Vol. 321, p. 37–40).

(5) $^{13}C$-NMR Spectrum $^{13}C$-NMR δ ($CD_3OD$): 18.018, 22.465, 26.078, 56.299, 92.289, 106.466, 109.730, 117.107, 124.560, 126.047, 128.582, 131.345, 132.529, 143.291, 161.399, 162.644, 164.981, 166.332, 193.928

(6) Infrared Spectrum (KBr method);

3280, 1705, 1606, 1541, 1512, 1470, 1439, 1346, 1292, 1227, 1171, 1144, 1103 $cm^{-1}$ (7) Mass Spectrum MS(EI) m/z: 354 ($M^+$), 339, 311, 299, 234, 219, 205, 191, 179, 177, 153, 147, 120

From the determination results of the spectra in the above items 4–7, the structural formula of xanthohumol was determined to be the structure of the above-mentioned formula (1).

Example 2

Determination of Bone Resorption Inhibiting Activity of Xanthohumol (1) Preparation of cell From 10 to 11-day old ICR mice (purchased from Charles River Inc.) were extracted femur and shank, which were then chopped using scissors in a-MEM medium (purchased from Flow Laboratories Inc.) containing 5% FBS (purchased from Irving Scientific Inc.), 100 U/ml penicillin and 100 µg/ml streptomycin. And further, the resulting supernatant was recovered by pipetting, washed with the medium and then suspended in 5% FBS, a-MEM medium to form bone cell containing osteoclasts. It was then adjusted to a cell level of $1 \times 10^7$/ml using the culture medium containing no rat parathyroid hormones.

(2) Assay using Pit Formation Assay

An ivory piece was cut to a thickness of 150 µm using a precision low speed cutter (purchased from Buehler GmbH) and then round pieces with a diameter of 6 mm cut out using a one-hole punch. These ivory pieces were immersed in 70% ethanol, subjected to sonication twice for 5 minutes each and then washed three times with sterile PBS and twice with the medium. These ivory pieces were placed in a 96-well culture plate (purchased from Falcon Inc.) and 100 µl of the medium containing medicaments at various concentrations (containing $2 \times 10^{-8}M$ rat parathyroid hormone) was added. Then, 100 µl of the medium containing the above prepared bone cells $1 \times 10^6$ was added to each well. Incubation was carried out at 37° C. in a 10% $CO_2$ incubator for 3 days. After completion of the incubation, the cell over the ivory piece was removed, absorption cavities were stained with Coomassie Brilliant Blue and the number of the absorption cavities thus formed was counted under microscope. The results are shown in Table 1.

TABLE 1

| Medicament conc. (M) | Number of absorption cavities (Mean + SD) | Inhibitory rate (%) |
| --- | --- | --- |
| 0 | 248.3 ± 35.7 | — |
| $10^{-4}$ | 0 | 100 |
| $10^{-5}$ | 15.8 ± 6.0 | 93.6 |
| $10^{-6}$ | 162.7 ± 41.2 | 34.5 |

As shown in the above Table, xanthohumol showed inhibitory values of as high as 100% at $1 \times 10^{-4}$M, 93.6% at $1 \times 10^{-5}$M and 34.5% at $1 \times 10^{-6}$M.

Consequently, it was confirmed that xanthohumol inhibits bone resorption at a concentration of as low as $10^{-6}$M.

What is claimed is:

1. A method for treating osteoporosis by inhibiting bone resorption associated therewith, which comprises administering to a human in need of such treatment a pharmaceutical composition containing, as an active ingredient, an effective amount of xanthohumol having the formula:

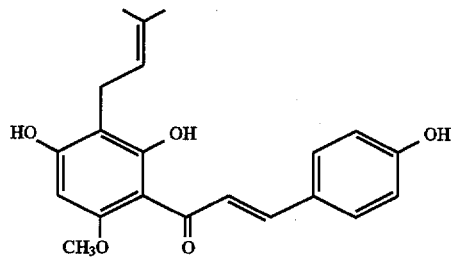

(1)

and a pharmaceutically acceptable carrier.

* * * * *

UNITED STATES PATENT AND TRADEMARK OFFICE
CERTIFICATE OF CORRECTION

PATENT NO. : 5,679,716
DATED : October 21, 1997
INVENTOR(S) : Hiroyasu TOBE et al.

It is certified that error appears in the above-indentified patent and that said Letters Patent is hereby corrected as shown below:

On the Title page, item [54]    and in Col. 1, line 1

"PHARMACEUTICAL COMPOSITION"
   should read --METHOD--.

Signed and Sealed this

Twelfth Day of May, 1998

Attest:

BRUCE LEHMAN

Attesting Officer    Commissioner of Patents and Trademarks